United States Patent [19]

Van Grinsven et al.

[11] Patent Number: 5,364,640

[45] Date of Patent: Nov. 15, 1994

[54] PROCESS FOR PRODUCING ALKYL-METHYL KETONES

[75] Inventors: Adrianus M. Van Grinsven, Oss; Alfons L. J. Peters; Robert Roos, both of Bussum; Andras J. Wieg, Amsterdam, all of Netherlands

[73] Assignee: Unilever Patent Holdings B.V., Rotterdam, Netherlands

[21] Appl. No.: 908,732

[22] Filed: Jul. 6, 1992

Related U.S. Application Data

[63] Continuation of Ser. No. 554,838, Jul. 20, 1990, abandoned.

[30] Foreign Application Priority Data

Jul. 27, 1989 [EP] European Pat. Off. ........ 89201977.9

[51] Int. Cl.$^5$ .................. A23D 9/00; A23L 1/221
[52] U.S. Cl. ................................. 426/33; 426/650
[58] Field of Search ............ 426/33, 42, 61, 650, 426/386, 387, 533, 534, 650

[56] References Cited

U.S. PATENT DOCUMENTS

| | | | |
|---|---|---|---|
| 3,100,153 | 8/1963 | Knight | 426/35 |
| 3,720,520 | 3/1973 | Luksas | 426/42 |
| 4,832,964 | 5/1989 | Pratt | 426/33 |
| 4,960,597 | 10/1990 | Farbood | 426/3 |

OTHER PUBLICATIONS

R. Lawrence "The Metabolism of Triglycerides by Spores of *Penicillium roqueforti*" Journal of General Microbiology, vol. 46, No. 1, Jan. 1967, pp. 65-76.

J. Okumura, et al., "Methyl Ketone Formation by *Penicilium camemberti* in Model Systems", Chemical Abstracts, vol. 102, No. 15, 15th Apr. 1985, p. 506, Abstract No. 1305574.

T. Yagi, et al. "Production of Ketoalkanes from Fatty Acid Esters by a Fungus, Trichoderma", Chemical Abstracts vol. 111, No. 25, 18th Dec. 1989, p. 413, Abstract No. 228749x.

*Primary Examiner*—Donald E. Czaja
*Assistant Examiner*—Leslie Wong
*Attorney, Agent, or Firm*—Cushman, Darby & Cushman

[57] ABSTRACT

The invention relates to a process for producing methyl-alkyl ketones using micro-organisms which convert fatty acids or their esters into the corresponding methyl ketones having one carbon atom less. Suitable micro-organisms are those which produce at least 0.1% w/w methylketones in the culture broth. Preferred micro-organisms are *Aureobasidium pullulans* species. The process is especially suitable to produce pentan-2-one, heptan-2-one, nonan-2-one and undecan-2-one or mixtures thereof. The compounds produced are suitable for use in food flavors.

8 Claims, No Drawings

PROCESS FOR PRODUCING ALKYL-METHYL KETONES

This is a continuation of application Ser. No. 07/554,838, filed on Jul. 20, 1990, now abandoned.

The invention concerns a process for producing alkyl-methyl ketones using a micro-organism cultured in a culture medium containing suitable fatty acids or esters thereof as the substrate. The invention also concerns mixtures comprising such alkyl-methyl ketones and the use of such ketones for flavouring foodstuffs.

BACKGROUND OF THE INVENTION

Several alkyl-methyl ketones are used in the flavour and the food industry for their organoleptic properties. Some of them are known to give an important contribution to cheese and dairy type flavours. For their application in flavourings and foodstuffs it is considered advantageous to produce these ketones by microbial fermentation.

It is known from U.S. Pat. Nos. 3,720,520 and 4,133,895 to produce cheese flavoured mixtures, including methyl ketones, by culturing *Penicillium roqueforti* in a fat, especially milk fat, containing culture medium. The use of *Penicillium camemberti* for this purpose is described in J. Dairy Sci. 68 (1985) pp. 11–15. Other fungi noted for their ability to convert fatty acids into methyl ketones are mentioned in U.S. Pat. No. 3,100,153 and include a large number of Penicillium and Aspergillus species. However, these microorganism species produce only very limited quantities of methylketones when grown on fatty acid glycerides and thus are preferable grown on lipolyzed fat or used in combination with a lipase, see e.g. U.S. Pat. No. 4,133,895. Even then, the prior art processes produce only moderate quantities of the desired ketones. Thus, there is a need for a process whereby the ketones can be obtained in high yield using either fatty acids, fatty acid esters or mixtures of these as the substrate, and whereby the ketones may be isolated in relatively concentrated form.

SUMMARY OF INVENTION

Now, a process has been found for producing methylalkyl ketones using microorganisms which when subjected to the productivity test described below produce at least 0.1% w/w methylketones in the culture broth. Preferred are those microorganisms which produce at least 0.65% w/w methylketones, in particular those which produce 1.0%.

Species of the genus *Aureobasidium pullulans* (also known as *Pullularia pullulans*) or teleomorphs thereof are especially preferred for the process according to the invention and have the added advantage of being easy to culture. According to recent classification some species of this group are sometimes classified as Hormonema. However, for the purposes of this invention such molds are all considered to belong to the genus *Aureobasidium pullulans*.

DETAILED DESCRIPTION OF INVENTION

The productivity test for selecting microorganisms according to this invention is carried out according to the following procedure:

A culture medium is prepared consisting of 33% w/w trubol (Henkel KGaA, Düsseldorf, BRD), 0.6% neutralized soy peptone (Oxoid L44) and 66.4% water. The pH of the medium is adjusted to 4.5 with 85% aqueous lactic acid and the medium is sterilized by heating at 121° C. for 20 minutes. After cooling to 25° C. sufficient inoculum (about 1% w/w) is added to cause the culture medium to contain about $10^5$ colony forming units per ml. 100 ml of this culture broth is cultured for 5 days at 25° C. in 250 ml flasks with baffles and shaken in an orbital shaker (Gallenkamp type INR200) with sufficient speed to form a proper emulsion en provide sufficient aeration (150 rpm). The content of methyl ketones is measured by taking 2 ml aliquots from the broth, adding 10 ml of acetone to each aliquot to obtain a homogeneous mixture and determine the amount of methyl ketones in the mixture by GLC.

In the process according to the invention the microorganism is cultured aerobically in a medium containing suitable fatty acids or esters thereof under conditions wherein it converts a fatty acid into the corresponding methyl ketone having one carbon atom less. Under these conditions the microorganism is also capable of hydrolysing fatty acid esters to the corresponding fatty acids.

The process is especially suitable for producing pentan-2-one, heptan-2-one, nonan-2-one and undecan-2-one and mixtures of two or more of these ketones from the corresponding fatty acids having on carbon atom more or from esters of these acids. Such esters include alkyl esters, especially ethyl esters, and mono-, di- or tri-glycerides and mixtures thereof. The di- and tri-glycerides may be derived from a single fatty acid or they may be mixed glycerides. Especially suitable are triglycerides, preferably those derived from animal or vegetable sources, such as coconut oil, milk fat or palm kernel oil. Preferably, *Aureobasidium pullulans* is cultured under conditions favouring the presence of blastospores, such as described by M. J. Sevilla et al, Trans. Br. mycol. Soc. 68 (2), (1977) 300–303 and D. Park, idem, 82 (1), (1984), 39–44; C. Pasquier-Clouet and J. Zucca, Ann. Inst. Pasteur/Microbiol. 1987, 138, 165–176; L. A. Cooper and G. M. Gadd, Antonie van Leeuwenhoek 50 (1984), 249–260. The pH of the culture broth is not critical but is suitably kept between 2 and 9, preferably between 3 and 8. The temperature should be kept at such a level that the microorganism is able to grow, suitably between 10° and 40° C. and preferable between 15° and 35° C. Suitable *Aureobasidium pullulans* strains may be obtained from known sources described in the literature or e.g. from scientific culture collections.

A suitable culture medium comprises the usual nutrients, i.e. carbon sources, nitrogen sources, inorganic salts, growth factors and trace elements. Suitable carbon sources are known in the art and include saccharides, and saccharide derived polyols, glycerol, organic acids, such as lactic acid, citric acid, succinic acid, ascorbic acid and the like. Among the suitable nitrogen sources are e.g. peptone, meat extract, yeast and yeast extract, malt extract, wort extract, corn steep liquor, amino-acids, ammonium salts and ureum. Preferably an inoculation suspension of the mold is prepared in a pre-culture to which a suitable amount of the fatty acid or fatty acid ester, which is used as the substrate, is added to aid the mold in adapting to the substrate. This pre-culture is preferably inoculated with $10^4$–$10^6$ cells/ml of culture medium and cultured for 12–48 hours, particularly 15–30 hours. This pre-culture is then used to inoculate the production culture, using 1–100 ml of pre-culture per liter of production culture medium.

The amount of substrate to be added to the culture medium depends on the nature of the substrate and its influence on the growth of the microorganism. Some substrates may be added in concentrations of 10% w/w or more. On the other hand some fatty acid substrates already prevent microorganism growth when present in a concentration of 5% or less. In such cases it may be advantageous to gradually add the substrate to the culture broth during the culturing process, e.g. using a fed-batch-type process, thereby continually keeping the substrate concentration below the limit which is deleterious to the growth of the microorganism.

When the substrate is a liquid fatty acid ester, the culture broth will generally be a two phase system, the non-aqueous or organic phase comprising the liquid fatty acid ester and the aqueous phase containing the water-soluble nutrients. The organic phase may be diluted with an organic solvent which is not toxic to the microorganism, such as a mineral or vegetable oil or a suitable hydrocarbon. If the substrate is a solid ester or a fatty acid it may be dissolved in a suitable organic solvent. The methyl ketones produced preferentially dissolve in the organic phase. To facilitate dispersion of the organic phase in the aqueous phase, a suitable emulsifier, such as lecithine, may be added in an amount of up to 0.1% w/w of the culture broth. Foaming of the culture broth may be prevented by the addition of conventional anti-foaming agents.

A level of 0.1% w/w of ketone in the culture broth is usually reached within 8–10 hours and the maximum amount is generally reached within 50–200 hours. The product ketone or ketones is/are usually obtained in a concentration of at least 0.65% w/w, but often ketones may be obtained in concentrations of 1% or more.

The ketones may be concentrated and/or separated from the culture broth with usual techniques, such as extraction with an organic solvent and/or separation of the organic phase. The ketones may then be isolated from the organic phase e.g. by distillation or steam distillation. Alternatively the ketones may be distilled or steam distilled directly from the culture broth. Any of these isolation procedures may optionally be combined with removal of the solid material by filtration or centrifugation. Recovered substrate may be recycled in the process.

The ketones or ketone mixtures produced according to the invention may be used as a flavour ingredients in flavourings and foodstuffs, either as such or dissolved in suitable solvent or processed into a powdered product. They will often also contain small quantities of other valuable flavour components derived from the microbial fermentation. They are especially suitable to impart cheese- or dairy-type flavour notes or to improve or strengthen such notes. Alternatively, any one of the intermediate stages of the isolation procedures mentioned above may be used as a ketone-rich ingredient for addition to flavourings or foodstuffs. When a relatively high ketone content is obtained in the culture broth, even the whole broth may be added to flavourings or foodstuffs either as such or after processing into a powdered product, e.g. by spray drying. The processing of part or the whole of the culture broth into a flavour ingredient should preferably include a pasteurization step.

Flavouring components which may be used in conjunction with the ketones or ketone containing mixtures obtained according to the invention are well known in the art and are mentioned e.g. in S. Arctander, Perfume and Flavor Materials of Natural Origin, Elizabeth, N.J., U.S.A. (1969), in T. E. Furia et al., CRC Fenaroli's Handbook of Flavor Ingredients, 2nd ed., Cleveland, CRC Press Inc. (1975) and in H. B. Heath, Source Book of Flavors, The Avi Publishing Co. Inc., Westport, Conn. (1981).

The invention is illustrated by the following examples but not in any way limited thereto.

EXAMPLE 1

A 1500 l fermentor was charged with 6 kg dextrose (AVEBE, Veendam, The Netherlands), 6 kg soy peptone (Oxoid L44), 100 kg corn oil (Verenigde Zetmeelbedrijven/Bijenkorf B. V., Koog a/d Zaan, The Netherlands), and 888 l water. The pH of the mixture was adjusted to 4.5 with 85% aqueous lactic acid and the mixture was then sterilized with steam for 20 minutes at 121° C. After cooling to 25° C. the mixture was inoculated aseptically with 10 kg of a preculture containing $10^7$ cells/ml of *Aureobasidium pullulans* (CBS 621.80, obtainable from Centraal Bureau v. Schimmelcultures P.O. Box 273, 3740 AG Baarn, the Netherlands). The mixture was agitated with aeration of about 0.2 l/l/min. at a temperature of 25° C. When the dextrose had disappeared (after about 16 hours) partly hydrolyzed coconut oil was added to the mixture at a rate of 15 l/hour for 24 hours (i.e. a total of 360 l). The fermentation was continued for another 32 hours after which the fermentation broth contained about 1.4% w/w of heptan-2-one, 0.4% nonan-2-one and 0.4% undecan-2-one, i.e. in total 2.2% w/w. The broth was pasteurized by heating at 80° C. for 20 minutes and the oil phase separated from the aqueous phase. The oil phase (365 kg) was used as a ketone rich flavour ingredient in cheese and dairy-type flavours.

EXAMPLE 2

A 100 l fermentor was charged with 33.2 l water, 16.5 kg of a mixture of $C_8$ and $C_{10}$ triglycerides (Trubol of Henkel KGaA, Düsseldorf) and 0.3 kg soy peptone (Oxoid L44). The pH of this mixture was adjusted to 4.5 with 85% aqueous lactic acid and thereafter the mixture was sterilized with steam for 20 minutes at 121° C. After cooling to 25° C. the mixture was inoculated aseptically with 0.63 kg of a preculture containing about 107 cells/ml of *Aureobasidium pullulans* CBS 621.80. The mixture was then agitated with aeration of about 0.2 l/l/min and at a temperature of about 25° C. for 4 days. By then the fermentation mixture contained about 2.4% w/w heptan-2-one and 0.6% w/w nonan-2-one (calculated on the weight of the fermentation broth). The broth was pasteurized by heating to 80° C. for 20 minutes and a mixture of 22.5 kg of maltodextrine (Paselli MD20 of AVEBE, Veendam, The Netherlands), 22.5 kg corn starch (Capsul of National Starch & Chem. Co., Zutphen, the Netherlands) and 45 kg water was added. The whole mixture was thoroughly mixed and spray-dried to yield 62 kg of a dry and free flowing flavour ingredient containing 1.9% w/w heptan-2-one and 0.5 % nonan-2-one which was successfully used as an ingredient for cheese flavours.

EXAMPLE 3

A 1500 l fermentor was charged with 664 l water, 330 kg of a mixture of $C_8$ and $C_{10}$ triglycerides (trubol of Henkel KGaA, Düsseldorf) and 6 kg soy peptone (Oxoid L44). The pH of this mixture was adjusted to 4.5 with 85% aqueous lactic acid and thereafter the mixture was sterilized with steam for 20 minutes at 121° C. After cooling to 25° C. the mixture was inoculated aseptically with 12.5 kg of a preculture containing about $10^7$ cells/ml of *Aureobasidium pullulans* (CBS 105.22). The mixture was then agitated with aeration of about 0.2 1/1/min and at a temperature of about 25° C. The fermentation was progressed for 24 hours and thereafter a mixture of 15 kg caproic acid (Wacker Chemie, München, BRD) and 50 kg trubol was added in a fed batch mode at a rate of 1.25 kg/hour. The fermentation was progressed for another 100 hours and by that time the fermentation broth contained about 1.1% w/w of pentan-2-one, 1.7% heptan-2-one and 0.2% nonan-2-one. The broth was heated to 80° C. for 20 minutes. The methyl ketones were isolated from the broth by steam distillation. 30 kg of a mixture of methyl ketones, also containing minor quantities of other valuable flavour components, was obtained.

EXAMPLE 4

A blue cheese flavour was prepared according to the following recipe:

|  | % by weight |
|---|---|
| Cheese powder | 45.00 |
| Lactic acid | 3.00 |
| Sodium chloride | 10.00 |
| Lactose | 15.70 |
| Monosodium glutamate | 8.00 |
| Caproic acid | 0.60 |
| Caprylic acid | 0.30 |
| Butyric acid | 0.30 |
| Propionic acid | 0.10 |
| Gamma-decalactone | 0.04 |
| Onion powder | 9.96 |
| Yeast extract (Gistex ex Distillers Co.) | 5.00 |
| Methylketone mixture according to EXAMPLE 2 | 2.00 |
|  | 100 |

This cheese flavour was sprinkled on freshly fried potato crisps in an amount of 6 g flavour per 100 g crisps. The crisps thus obtained a full and tasty blue cheese flavour.

We claim:

1. A process for producing methyl alkyl ketones comprising the steps of:
   a) selecting a species of the genus *Aureobasidium pullulans* that produces at least 0.1% w/w methyl alkyl ketones when subjected to a productivity test;
   b) culturing said species in a medium containing a substrate wherein said substrate consists of fatty acids or esters thereof, under conditions such that each methyl alkyl ketone produced contain one less carbon atom than said corresponding fatty acid or ester thereof.

2. A process according to claim 1, wherein pentan-2-one, heptan-2-one, nonan-2-one or undecan-2-one, or mixtures of two or more of these, are produced.

3. A process according to claim 2, wherein one or more fatty acids are used as the substrate.

4. A process according to claim 2, wherein mono-, di-, or triglycerides are used as the substrate.

5. A process according to claim 1 wherein the species is cultured under conditions favouring the presence of blastospores.

6. A process according to claim 3 wherein the substrate is added gradually to the culture medium so as to continually maintain a substrate concentration below the level which is toxic for the microorganism.

7. A process according to claim 1 wherein the culture medium comprises a liquid organic phase containing the substrate and an aqueous phase containing nutrients.

8. A process according to claim 1 wherein a species of the genus *Aureobasidium pullulans* is used which in the productivity test produces at least 0.65% methyl alkyl ketones in the culture broth.

* * * * *